US009790753B2

(12) United States Patent
Jamison et al.

(10) Patent No.: US 9,790,753 B2
(45) Date of Patent: Oct. 17, 2017

(54) FLEXURE MEMBRANE FOR DRILLING FLUID TEST SYSTEM

(71) Applicant: Halliburton Energy Services, Inc., Houston, TX (US)

(72) Inventors: Dale E. Jamison, Humble, TX (US); Kenneth Heidt Matthews, Kingwood, TX (US); Andrew David Vos, Spring, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 0 days.

(21) Appl. No.: 14/763,553

(22) PCT Filed: Oct. 14, 2013

(86) PCT No.: PCT/US2013/064794
§ 371 (c)(1),
(2) Date: Jul. 27, 2015

(87) PCT Pub. No.: WO2015/057182
PCT Pub. Date: Apr. 23, 2015

(65) Prior Publication Data
US 2015/0354300 A1 Dec. 10, 2015

(51) Int. Cl.
*E21B 49/10* (2006.01)
*E21B 21/08* (2006.01)
*G01N 33/28* (2006.01)

(52) U.S. Cl.
CPC ............ *E21B 21/08* (2013.01); *E21B 49/10* (2013.01); *G01N 33/2823* (2013.01)

(58) Field of Classification Search
CPC .................. E21B 21/08; E21B 49/10
(Continued)

(56) References Cited

U.S. PATENT DOCUMENTS 3,967,680 A * 7/1976 Jeter .......................... E21B 4/00
166/325
4,320,007 A * 3/1982 Hultsch ..................... B04B 3/02
210/376

(Continued)

FOREIGN PATENT DOCUMENTS

| WO | 2008118956 A1 | 10/2008 |
| WO | 2015057182 A2 | 4/2015 |
| WO | 2015122866 A2 | 8/2015 |

OTHER PUBLICATIONS

International Search Report and Written Opinion for PCT/US2013/064794 dated Jun. 12, 2015.

*Primary Examiner* — John Fitzgerald
*Assistant Examiner* — Rodney T Frank
(74) *Attorney, Agent, or Firm* — McDermott Will & Emery LLP

(57) ABSTRACT

A disclosed dynamic receiver includes a housing defining a receiver chamber and having a first end cap at one end of the housing and a second end cap at an opposing end of the housing, a flexure membrane arranged within the receiver chamber and providing a membrane wall having a first end that is closed and arranged adjacent a fluid inlet into the receiver chamber and a second end that is open and secured to an inner wall of the receiver chamber, and a piston assembly movably arranged in the receiver chamber and including a piston head and a piston rod extending axially from the piston head, wherein, as filtrate from a test fluid enters the fluid inlet, the filtrate acts on the flexure membrane such that hydraulic fluid disposed within the membrane cavity is displaced and thereby moves the piston assembly axially within the receiver chamber.

18 Claims, 2 Drawing Sheets

(58) Field of Classification Search
USPC .................................................. 73/152.25
See application file for complete search history.

(56) References Cited

U.S. PATENT DOCUMENTS

| | | |
|---|---|---|
| 4,446,726 A | 5/1984 | Hockenberry |
| 4,748,849 A | 6/1988 | Jamison et al. |
| 4,808,308 A * | 2/1989 | Flory ................. B04B 3/02 210/248 |
| 4,937,553 A * | 6/1990 | Juckenack ........... B60T 8/3675 336/30 |
| 5,786,528 A | 7/1998 | Dileo et al. |
| 7,410,581 B2 * | 8/2008 | Arnold ................. B01D 61/02 210/321.6 |
| 8,496,828 B2 * | 7/2013 | Johnson ................ B01D 63/02 210/500.23 |
| 2006/0175245 A1 * | 8/2006 | Gerteis ................. B04B 3/025 210/372 |
| 2008/0203016 A1 * | 8/2008 | Johnson ................ B01D 63/02 210/636 |
| 2009/0217776 A1 | 9/2009 | Jamison |

* cited by examiner

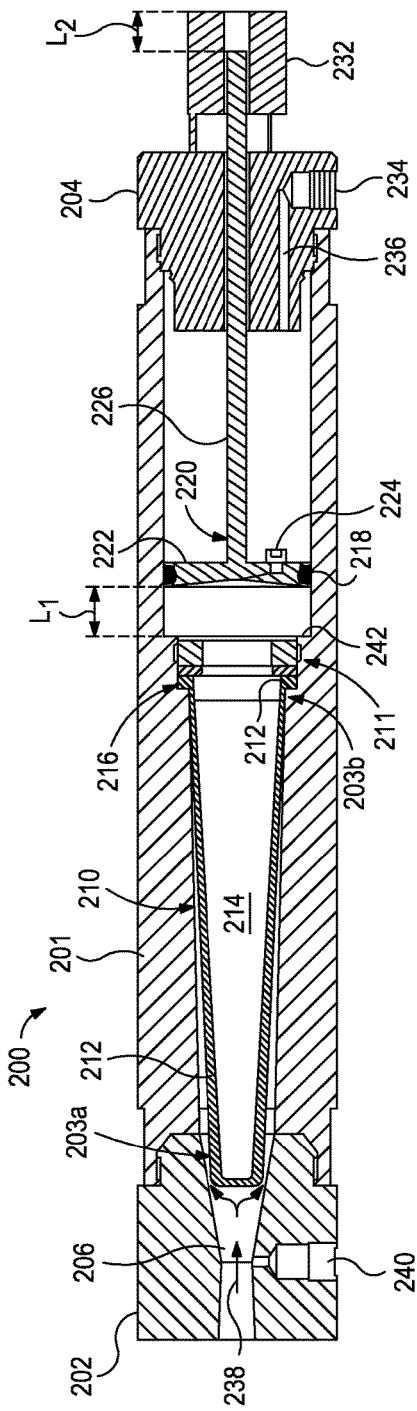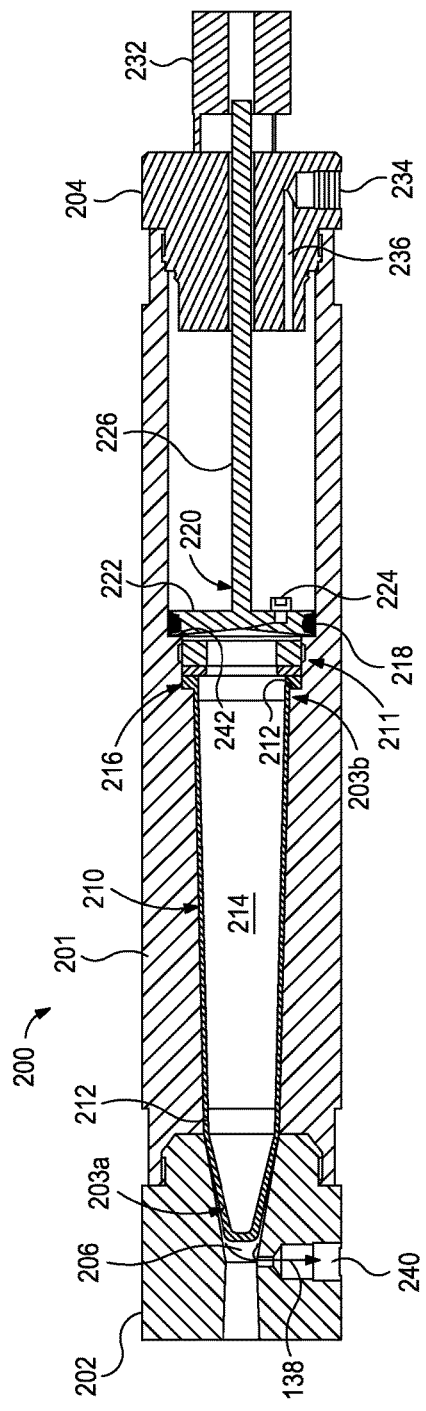

FLEXURE MEMBRANE FOR DRILLING FLUID TEST SYSTEM

BACKGROUND

The present disclosure is related to the testing of drilling fluids and, more particularly, to an apparatus and method for evacuating part of a fluid loss characteristics test system.

In drilling wellbores in the oil and gas industry, drilling fluid or "mud" is typically circulated into and out of the wellbore. The drilling fluid serves several purposes, such as lubricating the drill bit, cooling the drill bit, and removing the cuttings from the wellbore as the drill bit advances into the rock formation. To accomplish its intended purposes, the drilling fluid should ideally possess certain characteristics. For example, if desired, the drilling fluid should be capable of depositing a coating on the wall of the wellbore being drilled, the coating being commonly referred to as a filter cake. The filter cake serves to stabilize the wellbore and also prevent loss of the liquid portion of the drilling mud through the walls of the borehole into the adjoining rock formations. This loss of liquid from the drilling fluid is commonly referred to as fluid loss and encompasses a function of many variables such as the composition of the drilling fluid, the types of rock formations encountered while drilling, temperatures and pressures in the borehole, etc.

In order to ensure that a certain drilling fluid is able to operate as required or intended, drilling fluids are often tested under simulated borehole conditions in an attempt to determine characteristics of the drilling fluid, such as potential fluid loss. Common drilling fluid testing systems, however, require time-consuming disassembly and cleaning following each testing procedure.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIGS. 2A and 2B illustrate the apparatus of FIG. 1 in exemplary operation, according to one or more embodiments.

DETAILED DESCRIPTION

Figure 1:
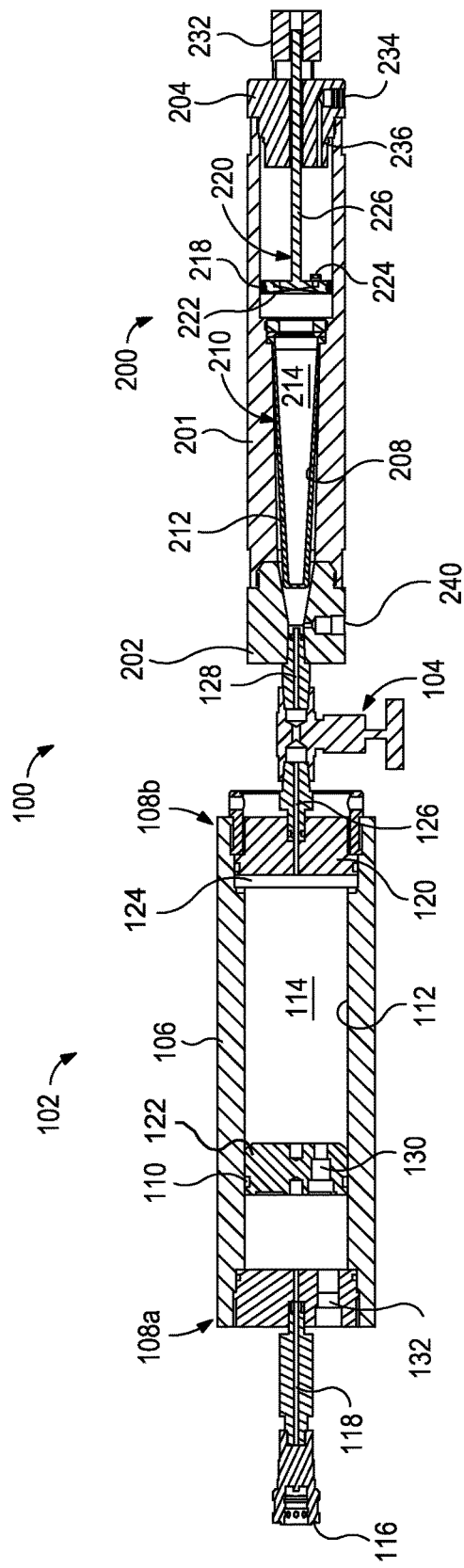
FIG. 1 is an exemplary apparatus for testing fluid loss characteristics, according to one or more embodiments.

The present disclosure is related to testing of drilling fluids and, more particularly, to an apparatus and method for evacuating part of a fluid loss characteristics test system.

The exemplary test system described in the present disclosure may be used to perform filtration or filtrate tests on fluids commonly used in the oil and gas industry, such as drilling fluids. The test system may incorporate or otherwise include a flexure membrane arranged within a dynamic receiver, the flexure membrane being capable of evacuating filtrate from the dynamic receiver after the completion of a test. In operation, the flexure membrane accomplishes such function by incorporating a design of tapered wall thickness, wherein the wall thickness is greatest at a first end of a receiver chamber where the filtrate enters, and gradually thins towards a second end of the receiver chamber. Using the flexure membrane, the filtrate can be evacuated from the dynamic receiver without disassembly and manual cleaning. Accordingly, incorporation of the flexure membrane may save an operator valuable time and cost in testing drilling fluids.

While the present disclosure is primarily focused on testing fluids related to the oil and gas industry, such as drilling fluids, those skilled in the art will readily appreciate that the embodiments discussed herein may equally be applied to other fields or technologies. For example, the systems and methods described herein may also be used to test fluids relating to the food industry, the mining industry, the agriculture industry, the medical industry, and the automotive industry.

Referring to FIG. 1, illustrated is an exemplary test fixture 100 that may be used in undertaking filtrate tests on a sample fluid, according to one or more embodiments of the present disclosure. Example uses of the test fixture 100 may include permeability plugging tests and lost circulation tests on the sample fluid. As illustrated, the test fixture 100 may include a test cell 102, a dynamic receiver 200, and a valve 104 that generally interposes the test cell 102 and the dynamic receiver 200 and allows fluid communication therebetween.

The test cell 102 may include a generally cylindrical body 106 having a proximal or first end 108a and a distal or second end 108b. A piston chamber 114 may be defined within the body 106 and may include an inner wall 112. At the first end 108a, the piston chamber 114 may be fluidly coupled to a pressure input valve 116 via an input conduit 118. An end cap 120 may be arranged or otherwise secured at the second end 108b of the body 106. In some embodiments, the end cap 120 may be threaded to the second end 108b, but may equally be attached thereto using one or more mechanical fasteners (e.g., screws, bolts, pins, snap rings, etc.).

A permeable filter medium 124 (hereinafter "filter 124") may be arranged within the piston chamber 114 and generally adjacent the end cap 120. In at least one embodiment, as illustrated, the filter 124 may be seated against or otherwise engage the end cap 120. The filter 124 may be intended to simulate the borehole wall, thus example compositions of the filter may include, but are not limited to, a porous or diatomaceous ceramic, paper, slots, strings, or sintered metals. 124

A piston 122 may be movably arranged within the piston chamber 114 and configured to translate axially therein. The piston may be sized or otherwise configured to sealingly engage the inner wall 112, possibly using one or more sealing devices 110, such as an O-ring, one or more dynamic sealing devices (e.g., v-packing seals), or the like. In one embodiment, the piston 122 may include a check valve or rupture disk 130 to prevent over-pressurization within the piston chamber 114. As depicted, the check valve or rupture disk 130 may be arranged within the piston 122 and otherwise configured to allow fluid flow from the distal end of the piston chamber 114 to the proximal end when the fluid pressure exceeds a predetermined threshold. In some embodiments, an additional check valve or rupture disk 132 may be included at or near the first end 108a of the body 106 and may be configured to allow fluids to exit the piston chamber 114 when the pressure within the piston chamber 114 exceeds a predetermined threshold.

The test cell 102 may further include a filtrate output conduit 126 defined within the end cap 120 and generally extending from the filter 124 to the valve 104. Accordingly, the valve 104 may be fluidly coupled to the piston chamber 114 via the filtrate output conduit 126, thereby allowing any filtrate passing through the filter 124 to exit the test cell 102 during testing operations.

The valve 104 may place the test cell 102 and the dynamic receiver 200 in fluid communication. More particularly, the test cell 102 may further include a filtrate input conduit 128 that leads into the dynamic receiver 200 and is otherwise in fluid communication with the filtrate output conduit 126 via the valve 104. The valve 104 may be movable between a first or "closed" position and a second or "open" position. In the first position, fluid communication between the test cell 102 and the dynamic receiver 200 is entirely or substantially prevented. The valve 104 may be placed in the first position, for example, prior to running a test procedure, thereby allowing each of the test cell 102 and dynamic receiver 200 to be independently configured and set. In the second position, fluid communication is allowed between the test cell 102 and the dynamic receiver 200 such that any filtrate that passes through the filter 124 may enter the dynamic receiver 200.

The dynamic receiver 200 may include a housing 201, a first end cap 202 arranged at one end of the housing 201, a second end cap 204 arranged at an opposing end of the housing 201, and a receiver chamber 208 defined within the housing 201. As illustrated, the filtrate input conduit 128 may be defined in or otherwise extend through the first end cap 202. An exit port 240 may also be defined in the first end cap 202 and may enable filtrate to exit the receiver chamber 208 following a test. The second end cap 204 may include or otherwise define an input port 234 and associated input conduit 236. Portions of the receiver chamber 208 may be pressurized via the input port 234 and its associated input conduit 236.

A flexure membrane 210 may be secured or otherwise arranged within the receiver chamber 208 and may include a membrane wall 212 that exhibits a thickness that changes along its length. As discussed in greater detail below, the thickness of the membrane wall 212 may be greatest near the first end cap 202 and may be less thick in the direction of the second end cap 204. The membrane wall 212 may further define a membrane cavity 214 within the flexure membrane 210. A hydraulic or incompressible fluid may be disposed within the membrane cavity 214. For example, the hydraulic fluid disposed within the membrane cavity 214 may include, but is not limited to, silicon oil, mineral oil, or water.

The dynamic receiver 200 may further include a piston assembly 220 movably arranged within the receiver chamber 208. As illustrated, the piston assembly 220 may include a piston head 222 and a piston rod 226 extending axially from the piston head 222. The piston assembly 220 may be configured to translate axially within the receiver chamber 208 in response to changes in pressure experienced on either side of the piston head 222.

In operation, the piston head 222 may be configured to dynamically seal against the inner wall of the receiver chamber 208 as piston assembly 220 translates axially therein. For instance, the piston head 222 may include one or more sealing devices 218 configured to provide a sealed interface between the inner wall of the receiver chamber 208 and the piston head 222. In one embodiment, the sealing device 218 may be a low squeeze O-ring or the like. In other embodiments, the sealing device 218 may include any other dynamic sealing device or mechanism, such as packing seal rings, or the like. As will be appreciated, the sealed interface of the piston head 222 may serve to isolate the fluids disposed within the membrane cavity 214 of the flexure membrane 210 from any fluids disposed on the opposite side of the piston head 222.

In one embodiment, the piston head 222 may further include a bleed valve 224 in fluid communication with the membrane cavity 214. The bleed valve 224 may be used, for example, to evacuate any gases that may be present in the hydraulic fluid disposed within the membrane cavity 214.

The piston rod 226 of the piston assembly 220 extends from the piston head 222 and through the second end cap 204. In at least one embodiment, the piston rod 226 may sealingly engage the second end cap, so as to provide a fluid-tight, dynamic seal. The piston rod 226 may further extend into and otherwise be received by a measurement device 232 that may be operatively coupled to the second end cap 204. As depicted, the measurement device 232 may be arranged external to the dynamic receiver 200. However, internal measurement devices 232 are also contemplated in the present disclosure. The measurement device 232 may be configured to measure the general displacement of the piston rod 226 and may include, for example, a linear potentiometer, string potentiometer, an optical displacement sensor, a linear variable differential transformer (LVDT), or an inductive proximity sensor.

In exemplary operation of the test fixture 100, a test fluid may be introduced into the piston chamber 114 of the test cell 102 between the piston 122 and the filter 124. Prior to testing, the valve 104 is closed such that fluid communication between the test cell 102 and the dynamic receiver 200 is generally prevented. The piston chamber 114 may then be pressurized via the pressure input valve 116 and associated input conduit 118. In some embodiments, the piston chamber 114 may simultaneously be heated so as to simulate desired temperature conditions. Once predetermined pressure and temperature parameters are achieved within the piston chamber 114, the valve 104 may be moved to the open position, thereby allowing fluid communication between the test cell 102 and the dynamic receiver 200.

A pressure differential exists between the test cell 102 and the dynamic receiver 200, and the pressure communicates with and otherwise acts on the test fluid such that a portion thereof (i.e., filtrate) permeates the filter 124 and exits the test cell 102 via the filtrate output conduit 126. The filtrate is able to pass through the valve 104 and into the receiver chamber 208 of the dynamic receiver 200 via the filtrate input conduit 128. The filtrate entering the receiver chamber 208 acts on and otherwise compresses the flexure membrane 210, thereby displacing a portion of the hydraulic fluid disposed within the membrane cavity 214. The displaced hydraulic fluid acts on and serves to move the piston assembly 220 axially within the receiver chamber 208. As the piston assembly 220 moves, the measurement device 232 may be configured to monitor and otherwise measure the distance traveled by the piston rod 226. Formulas known to those skilled in the art may then be employed to determine the volume of filtrate introduced into the receiver chamber 208. From such determinations, the filtration rate of the sample fluid through the filter 124 may then be surmised for consideration.

Referring now to FIGS. 2A and 2B, illustrated are cross-sectional side views of the dynamic receiver 200 of FIG. 1, according to one or more embodiments. More particularly, FIG. 2A depicts the dynamic receiver 200 in a first or relaxed position, such as prior to or at the beginning of a test procedure, and FIG. 2B depicts the dynamic receiver 200 in a second or evacuating position following a test procedure.

The flexure membrane 210 (or the membrane wall 212) may include a first end 203a and a second end 203b, where the first end 203a is closed and the second end 203b is generally open to the interior of the receiver chamber 208. The first end 203a may be configured to extend into or otherwise be arranged adjacent a filtrate inlet 206 defined within the first end cap 202. The filtrate inlet 206 may be configured to receive the filtrate from the valve 104 and is otherwise in fluid communication with portions of the receiver chamber 208. For clarity, the valve 104 and its associated filtrate input conduit 128 (FIG. 1) have been removed from the filtrate inlet 206 but would otherwise be fluidly coupled thereto.

At the second end 203b, the flexure membrane 210 may define or otherwise provide an annular lip or flange 216. The flange 216 may be configured to seat against a radial shoulder 242 defined within the receiver chamber 208. In one or more embodiments, the flange 216 may be secured in place against the radial shoulder 242 using one or more fastening mechanisms 211 such as, but not limited to, threaded washers, cylinder nuts, snap rings, or the like. The annular flange 216 may be compressed into the radial shoulder 242 using the fastening mechanism(s) 211 such that a generally sealed interface results. Accordingly, any fluids entering the filtrate inlet 206 and migrating into the receiver chamber 208 are substantially prevented from passing the annular flange 216. Moreover, the fastening mechanism(s) 211 may be annular, such that the hydraulic fluid within the membrane cavity 214 may be able to flow therethrough and otherwise interact with the piston assembly 220, as discussed above.

As best seen in FIG. 2A, the membrane wall 212 of the flexure membrane 210 may change in thickness or width from the first end 203a to the second end 203b. More particularly, the thickness of the membrane wall 212 at or near the first end 203a may be greater than the thickness of the membrane wall 212 at or near the second end 203b. In some embodiments, the thickness of the membrane wall 212 may progressively or gradually taper from the first end 203a to the second end 203b. In other embodiments, the thickness of the membrane wall 212 may intermittently or irregularly decrease from the first end 203a to the second end 203b, without departing from the scope of the disclosure. As will be appreciated, the variable thickness of the membrane wall 212 provides increased resistivity to expansion at the first end 203a as opposed to the second end 203b.

To further assist in the expansion of the membrane wall 212, the flexure membrane 210 may be made of one or more pliable or otherwise elastomeric materials including, but not limited to, polymeric materials, synthetic elastomers and rubbers (e.g., VITON®), silicon rubber, and the like. In some embodiments, selection of suitable materials for the flexure membrane 210 may depend on chemical and temperature compatibility with the sample fluid being tested and, more particularly, with the filtrate that is expected to contact the flexure membrane 210 during testing.

As mentioned above, the input port 234 may be defined in the second end cap 204 and may be configured to provide a gas or a liquid (i.e., any fluid) into the receiver chamber 208 via the conduit 236. Example gases that may be introduced into the receiver chamber 208 via the input port 234 and the conduit 236 may include, but are not limited to, nitrogen, carbon dioxide, air, or any other gas desirable to best effectuate a test procedure by one of skill in the art. Example liquids may include, but are not limited to, oils (e.g., silicon oil or mineral oil) or water. The gas(es) or liquid(s) (i.e., fluids) introduced into the receiver chamber 208 via the input port 234 may be configured to regulate the overall pressure conditions within the receiver chamber 208.

In conjunction with the testing procedure generally discussed above with reference to FIG. 1, a more detailed description of the exemplary operation of the dynamic receiver 200 will now be provided. Prior to undertaking a test of the sample fluid in the test cell 102 (FIG. 1), the dynamic receiver 200 may be configured in its first or relaxed position, as depicted in FIG. 2A. The receiver chamber 208 may be pressurized to a predetermined pressure with gas(es) or liquid(s) introduced thereto via the input port 234 and the conduit 326. In some embodiments, the receiver chamber 208 may be pressurized to a pressure of about 500 psi or greater. In other embodiments, the receiver chamber 208 may be pressurized to a pressure of less than 500 psi.

As generally depicted in FIG. 2A, once the valve 104 (FIG. 1) is moved into the open position, filtrate 238 from the higher pressure test cell 102 may be drawn into or otherwise introduced into the lower pressure dynamic receiver 200 and, more particularly, into the filtrate inlet 206. From the filtrate inlet 206, the filtrate 238 may be able to extend into or otherwise be received by portions of the receiver chamber 208 surrounding the flexure membrane 210. More specifically, as the filtrate 238 enters the dynamic receiver 200, it may first impinge upon or otherwise come into contact with the first end 203a of the flexure membrane 210. Filtrate 238 may also flow around the first end 203a and about the exterior of the membrane wall 212 towards the second end 203b of the flexure membrane 210.

As the filtrate 238 flows around the exterior of the membrane wall 212, the flexure membrane 210 is compressed, thereby decreasing the volume of the membrane cavity 214 and simultaneously displacing a portion of the hydraulic fluid disposed therein toward the piston assembly 220. The hydraulic fluid from the membrane cavity 214 may act on the piston head 222, thereby forcing the piston assembly away from the flexure membrane and otherwise axially towards the second end cap 204. The initial position of the piston head 222 may be known within the receiver chamber 208, depicted in FIG. 2A as a distance $L_1$ from a radial shoulder 242 defined in the receiver chamber 208. As the piston assembly 220 moves within the receiver chamber 208, the piston rod 226 may correspondingly move a distance of $L_2$, as measured and calculated by the measurement device 232. Using the now-known distance $L_2$ that the piston rod 226 has traveled and the overall operating parameters of the test fixture 100 (i.e., pressures, volumes, etc.), formulas known to those skilled in the art may then be employed to determine the volume of filtrate 238 introduced into the receiver chamber 208 from the test cell 102 (FIG. 1). From such determinations, the filtration rate of the sample fluid through the filter 124 may then be calculated.

Following a testing procedure, or in between testing procedures, it may be desirable to evacuate the filtrate 238 from the receiver chamber 208 so that the dynamic receiver 200 is able to return to its relaxed state. Such a process may be accomplished by first closing the valve 104 (FIG. 1), which will prevent backflow of the filtrate 238 into the test cell 102 as it is evacuated from the dynamic receiver 200. The receiver chamber 208 may then be pressurized with a gas or liquid introduced through the input port 234 and the conduit 236. The increasing pressure within the receiver chamber 208 acts upon the piston head 222 such that the piston assembly 220 is forced to move axially towards the radial shoulder 242. As a result, the hydraulic fluid is correspondingly conveyed back into the membrane cavity 214.

Referring now to FIG. 2B, continued application of fluid pressure into the receiver chamber 208 via the input port 234 and the conduit 236 may correspondingly force the piston head 222 against or otherwise adjacent the radial shoulder 242. Forcing the piston head 222 to (or adjacent to) the radial shoulder 242 may correspondingly cause the hydraulic fluid within the membrane cavity 214 to force the membrane wall 212 against the inner walls of the receiver chamber 208 surrounding the flexure membrane 210.

Advantageously, the thinner portions of the membrane wall 212 may be configured to expand prior to the thicker portions of the membrane wall 212. As a result, the hydraulic force derived from the hydraulic fluid being forced against the membrane wall will have a greater initial effect on the portions of the membrane wall 212 at or near the second end 203b of the flexure membrane 210, thereby allowing such portions to expand first, followed by a gradual expansion of the membrane wall 212 proceeding toward the first end 203a. The membrane wall 212 may be configured to expand until it engages the inner wall of the receiver chamber 208, thereby progressively squeezing or otherwise forcing any filtrate 238 present between the membrane wall 212 and the inner wall of the receiver chamber 208 out towards the filtrate inlet 206 or otherwise towards the first end cap 202. In other words, as pressure builds within the membrane cavity 214, the thinner portions of the membrane wall 212 will expand first, gradually and continually expanding through the thicker portions of the membrane wall 212 toward the first end 203a. Thus, any filtrate 238 that may have infiltrated into the receiver chamber 208 about the exterior of the membrane wall 212 will correspondingly be gradually forced out of the receiver chamber 208 towards the filtrate inlet 206.

Once in the filtrate inlet 206, the filtrate 238 squeezed out of the receiver chamber 138 may exit the dynamic receiver 200 via the exit port 240 defined within the first end cap 202. Outflow of the filtrate 238 may continue until the flexure membrane 210 displaces or otherwise squeezes out all or a substantial portion of the filtrate 238 drawn into the receiver chamber 208 during the testing procedure.

One of skill in the art will readily appreciate that use of such dynamic techniques to evacuate the receiver chamber 208 reduces the necessity to remove and clean the dynamic receiver 200 between test procedures. Accordingly, the receiver chamber 208 may be fully or substantially evacuated of filtrate 238 following each sample fluid testing without requiring manual disassembly and/or laborious cleaning of the dynamic receiver 200 prior to running another sample fluid test. Furthermore, when full disassembly and cleaning is required or otherwise desired, the presently disclosed embodiments will require less overall cleaning. More particularly, the filtrate 238 is substantially removed from the receiver chamber 208, as generally described above, and the flexure membrane 210 serves to isolate most of the receiver chamber 208 from the influx of filtrate 238. As a result, the filtrate 238 is unable to contaminate or otherwise damage electronics or other sensitive equipment that may be associated with the receiver chamber 208. Moreover, friction of the piston assembly 220 is kept low since filtrate 238 is unable to contaminate the sealing devices 218.

Embodiments disclosed herein include:

A. A dynamic receiver that includes a housing defining a receiver chamber and having a first end cap at one end of the housing and a second end cap at an opposing end of the housing, a flexure membrane arranged within the receiver chamber and providing a membrane wall that defines a membrane cavity therein, wherein the membrane wall has a first end that is closed and arranged adjacent a fluid inlet into the receiver chamber and a second end that is open and secured to an inner wall of the receiver chamber, and a piston assembly movably arranged in the receiver chamber adjacent the second end and including a piston head and a piston rod extending axially from the piston head, wherein, as filtrate from a test fluid enters the fluid inlet, the filtrate acts on the flexure membrane such that hydraulic fluid disposed within the membrane cavity is displaced and thereby moves the piston assembly axially within the receiver chamber.

B. A method of receiving a filtrate from a test fluid into a receiver chamber defined within a housing of a dynamic receiver, compressing a membrane wall of a flexure membrane arranged within the receiver chamber with the filtrate, the membrane wall defining a membrane cavity and having a first end that is closed and a second end that is open and secured to an inner wall of the receiver chamber, displacing a hydraulic fluid from the membrane cavity as the filtrate compresses the flexure membrane, and axially moving a piston assembly arranged within the receiver chamber with the hydraulic fluid, the piston assembly including a piston head and a piston rod extending axially from the piston head.

C. A test fixture that includes a test cell defining a piston chamber and having a filter medium arranged therein, wherein the filter medium filters a test fluid under pressure such that filtrate is able to exit the test cell, a dynamic receiver in fluid communication with the test cell and defining a receiver chamber therein, the dynamic receiver having a flexure membrane arranged within the receiver chamber and providing a membrane wall that defines a membrane cavity therein, wherein the membrane wall has a first end that is closed and arranged adjacent a fluid inlet into the receiver chamber and a second end that is open and secured to an inner wall of the receiver chamber, a piston assembly movably arranged in the receiver chamber adjacent the second end and including a piston head and a piston rod extending axially from the piston head, and a measuring device operatively coupled to the dynamic receiver and configured to measure axial displacement of the piston assembly within the receiver chamber, wherein the filtrate enters the fluid inlet and acts on the flexure membrane such that a hydraulic fluid disposed within the membrane cavity is displaced and thereby moves the piston assembly axially within the receiver chamber.

Each of embodiments A, B, and C may have one or more of the following additional elements in any combination: Element 1: wherein the fluid inlet is defined in the first end cap. Element 2: wherein a thickness of the membrane wall is greater at the first end than at the second end. Element 3: wherein the thickness progressively tapers from the first end to the second end. Element 4: wherein the thickness irregularly decreases from the first end to the second end. Element 5: wherein the flexure membrane comprises a material selected from the group consisting of polymers, elastomers, rubbers, synthetic elastomers, and synthetic rubbers. Element 6: further comprising a measuring device configured to measure axial displacement of the piston assembly within the receiver chamber. Element 7: further comprising a flange defined at the second end of the membrane wall, and one or more fastening mechanisms used to secure the flange against a radial shoulder defined within the receiver chamber and thereby generate a sealed interface. Element 8: further comprising an input port and a conduit each defined in the second end cap and configured to facilitate introduction of a fluid, and thereby pressurize the receiver chamber, and an exit port defined in the first end cap, wherein, as the receiver chamber is pressurized, the piston assembly is moved and forces the hydraulic fluid back into the membrane cavity, thereby pushing the membrane wall against the inner wall of the receiver chamber and, wherein, as the membrane wall is pushed against the inner wall of the receiver chamber, the filtrate is squeezed out of the receiver chamber and exits the dynamic receiver via the exit port.

Element 9: further comprising measuring axial displacement of the piston assembly within the receiver chamber with a measuring device. Element 10: wherein compressing the flexure membrane further comprises flowing filtrate about an exterior of the membrane wall toward the second end of the flexure membrane. Element 11: further comprising forcing the piston assembly away from the flexure membrane with the hydraulic fluid. Element 12: further comprising introducing a fluid into the receiver chamber, and thereby pressurizing the receiver chamber, moving the piston assembly axially toward the flexure membrane with the fluid, and thereby forcing the hydraulic fluid back into the membrane cavity, forcing the membrane wall against the inner wall of the receiver chamber with the hydraulic fluid, and squeezing the filtrate out of the receiver chamber as the membrane wall is forced against the inner wall of the receiver chamber. Element 13: further comprising evacuating the filtrate out of the dynamic receiver via an exit port defined in a first end cap arranged on the housing. Element 14: wherein a thickness of the membrane wall is greater at the first end than at the second end, and wherein forcing the membrane wall against the inner wall of the receiver chamber further comprises expanding portions of the membrane wall at the second end to the inner wall prior to expanding portions of the membrane wall at the first end, and forcing the filtrate out of the receiver chamber from the second end to the first end.

Element 15: wherein a thickness of the membrane wall is greater at the first end than at the second end. Element 16: wherein the thickness progressively tapers from the first end to the second end. Element 17: wherein the thickness irregularly decreases from the first end to the second end.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A dynamic receiver used in filtration testing, comprising:
    a housing defining a receiver chamber between opposing first and second ends of the housing;
    a flexure membrane arranged within the receiver chamber and defining a membrane cavity, the flexure membrane having a first end that is closed and arranged adjacent a fluid inlet into the receiver chamber and a second end that is open and secured to an inner wall of the receiver chamber;
    a piston arranged in the receiver chamber adjacent the second end of the flexure membrane; and
    a measuring device that measures axial displacement of the piston,
    wherein filtrate originating from a test fluid enters the receiver chamber at the fluid inlet and acts on the flexure membrane to displace hydraulic fluid from within the membrane cavity, and the hydraulic fluid acts on and moves the piston, and wherein a filtration rate of the test fluid is determined based on the axial displacement of the piston.

2. The dynamic receiver of claim 1, further comprising a first end cap coupled at the first end of the housing, wherein the fluid inlet is defined in the first end cap.

3. The dynamic receiver of claim 1, wherein a thickness of the flexure membrane is greater at the first end than at the second end.

4. The dynamic receiver of claim 3, wherein the thickness progressively tapers from the first end to the second end.

5. The dynamic receiver of claim 3, wherein the thickness irregularly decreases from the first end to the second end.

6. The dynamic receiver of claim 1, wherein the flexure membrane comprises a material selected from the group consisting of polymers, elastomers, rubbers, synthetic elastomers, and synthetic rubbers.

7. The dynamic receiver of claim 1, further comprising:
    a flange defined at the second end of the flexure membrane; and
    one or more fastening mechanisms that secure the flange against a radial shoulder defined within the receiver chamber and thereby generate a sealed interface.

8. The dynamic receiver of claim 1, further comprising:
    a first end cap coupled at the first end of the housing and defining an exit port; and
    a second end cap coupled at the second end of the housing and defining an input port and a conduit configured to facilitate introduction of a fluid into the receiver chamber, and thereby pressurize the receiver chamber, wherein, as the receiver chamber is pressurized, the piston is moved and forces the hydraulic fluid into the membrane cavity, thereby pushing the flexure membrane against the inner wall of the receiver chamber and, wherein, as the flexure membrane is pushed against the inner wall of the receiver chamber, the filtrate is squeezed out of the receiver chamber and exits the dynamic receiver via the exit port.

9. A method for filtration testing, comprising:
receiving filtrate originating from a test fluid into a receiver chamber defined within a housing of a dynamic receiver, the housing having a flexure membrane arranged within the receiver chamber and the flexure membrane defining a membrane cavity and having a first end that is closed and a second end that is open and secured to an inner wall of the receiver chamber;
compressing the flexure membrane with the filtrate and thereby displacing a hydraulic fluid from the membrane cavity;
acting on a piston arranged within the receiver chamber with the hydraulic fluid displaced from the membrane cavity; and
measuring axial displacement of the piston with a measuring device and thereby determining a filtration rate of the test fluid.

10. The method of claim 9, wherein compressing the flexure membrane further comprises flowing filtrate about an exterior of the flexure membrane toward the second end of the flexure membrane.

11. The method of claim 9, further comprising forcing the piston away from the flexure membrane with the hydraulic fluid.

12. The method of claim 9, further comprising:
introducing a fluid into the receiver chamber, and thereby pressurizing the receiver chamber;
moving the piston axially toward the flexure membrane with the fluid, and thereby forcing the hydraulic fluid back into the membrane cavity;
forcing the flexure membrane against the inner wall of the receiver chamber with the hydraulic fluid; and
squeezing the filtrate out of the receiver chamber as the flexure membrane is forced against the inner wall of the receiver chamber.

13. The method of claim 12, further comprising evacuating the filtrate out of the dynamic receiver via an exit port defined in a first end cap arranged on the housing.

14. The method of claim 12, wherein a thickness of the flexure membrane is greater at the first end than at the second end, and wherein forcing the flexure membrane against the inner wall of the receiver chamber further comprises:
expanding portions of the flexure membrane at the second end to the inner wall prior to expanding portions of the flexure membrane at the first end; and
forcing the filtrate out of the receiver chamber from the second end of the flexure membrane to the first end of the flexure membrane.

15. A test fixture for filtration testing, comprising:
a test cell defining a piston chamber and having a filter medium arranged therein to filter a test fluid under pressure such that filtrate from the test fluid is able to exit the test cell;
a dynamic receiver in fluid communication with the test cell and defining a receiver chamber, the dynamic receiver having a flexure membrane arranged within the receiver chamber and defining a membrane cavity, the flexure membrane having a first end that is closed and arranged adjacent a fluid inlet into the receiver chamber and a second end that is open and secured to an inner wall of the receiver chamber;
a piston arranged in the receiver chamber adjacent the second end of the flexure membrane; and
a measuring device operatively coupled to the dynamic receiver to measure axial displacement of the piston,
wherein the filtrate enters the receiver chamber at the fluid inlet and acts on the flexure membrane to displace hydraulic fluid from within the membrane cavity, and the hydraulic fluid acts on and moves the piston, and wherein a filtration rate of the test fluid is determined based on the axial displacement of the piston.

16. The test fixture of claim 15, wherein a thickness of the flexure membrane is greater at the first end than at the second end.

17. The test fixture of claim 16, wherein the thickness progressively tapers from the first end to the second end.

18. The test fixture of claim 16, wherein the thickness irregularly decreases from the first end to the second end.

* * * * *